US00PP35497P2

(12) United States Plant Patent
Menzel

(10) Patent No.: US PP35,497 P2
(45) Date of Patent: Nov. 21, 2023

(54) ***MISCANTHUS* PLANT NAMED 'GENTLE BREEZE'**

(50) Latin Name: *Miscanthus sinensis*
Varietal Denomination: Gentle Breeze

(71) Applicant: Klaus Menzel, Woellstein (DE)

(72) Inventor: Klaus Menzel, Woellstein (DE)

( * ) Notice: Subject to any disclaimer, the term of this patent is extended or adjusted under 35 U.S.C. 154(b) by 0 days.

(21) Appl. No.: 18/186,165

(22) Filed: Mar. 18, 2023

Related U.S. Application Data

(60) Provisional application No. 63/351,884, filed on Jun. 14, 2022.

(51) Int. Cl.
*A01H 5/12* (2018.01)
*A01H 6/46* (2018.01)

(52) U.S. Cl.
USPC ..... Plt./384
CPC ..... *A01H 6/46* (2018.05)

(58) Field of Classification Search
USPC ..... Plt./384
CPC ..... A01H 6/46; A01H 5/12
See application file for complete search history.

*Primary Examiner* — Keith O. Robinson
(74) *Attorney, Agent, or Firm* — Weatherly IP Solutions, LLC; James M. Weatherly

(57) ABSTRACT

A new and distinct cultivar of *Miscanthus* plant named 'Gentle Breeze' that is characterized by an upright plant habit, arching foliage which turns intense orange-red in October, and flowers which are silky silver-white in appearance, is disclosed. In combination, these traits set 'Gentle Breeze' apart from all other existing varieties of *Miscanthus* known to the inventor.

3 Drawing Sheets

Genus and species: *Miscanthus sinensis.*
Variety denomination: 'Gentle Breeze'.

BACKGROUND OF THE NEW PLANT

The present invention relates to a new and distinct cultivar of *Miscanthus*, also known as Maiden Grass, which is grown as an ornamental plant for use in the garden and landscape. The new cultivar is known botanically as *Miscanthus sinensis* and will be referred to hereinafter by the cultivar name 'Gentle Breeze'. The genus *Miscanthus* is included in the plant family Poaceae.

'Gentle Breeze' was discovered in 2004 as an open-pollinated seedling which was growing in the inventor's garden in Woellstein, Germany. At that time, the inventor had established six or seven varieties of *Miscanthus* in his garden. The inventor believes that two of these varieties are the unknown parents of the open-pollinated seedling, 'Gentle Breeze'.

The inventor observed that the new variety 'Gentle Breeze' was a significantly lower growing form of *Miscanthus* with mounding and arching narrow silver-green foliage which turns mauve and then deep red from late summer into fall. In addition, 'Gentle Breeze' bears delicate silver-white panicles of flowers from July to October.

Asexual propagation of 'Gentle Breeze' was first accomplished by the inventor in 2016 at the inventor's garden in Woellstein, Germany. The method of propagation used was division of the entire in-ground plant. Since that time under careful observation the inventor has determined that the characteristics of 'Gentle Breeze' are fixed, uniform, and true to type in all subsequent generations of asexual propagation.

SUMMARY

The following traits have been repeatedly observed and represent the distinguishing characteristics of the new *Miscanthus* cultivar 'Gentle Breeze'. These traits in combination set 'Gentle Breeze' apart from all other existing varieties of *Miscanthus* known to the inventor. 'Gentle Breeze' has not been tested under all possible conditions and phenotypic differences may be observed with variations in environmental, climatic and cultural conditions, however, without any variance in genotype.

1. 'Gentle Breeze' exhibits an upright low-growing plant habit with graceful arching foliage.
2. After one year's growth in a container, 'Gentle Breeze' is approximately 1.1 meters in height and 40 cm in width, including the height and width of the panicle of flowers.
3. The leaves of 'Gentle Breeze' are bicolored in spring and summer, consisting of a white to pale green central longitudinal stripe between two mid-green marginal bands.
4. The leaves of 'Gentle Breeze' begin to develop mauve and then eventually dark red colors from late summer into fall.
5. 'Gentle Breeze' bears delicate panicles of light mauve to silver-white flowers from July to October.
6. The flowers of 'Gentle Breeze' extend to a height of 50 cm above the bulk of the foliage canopy.
7. 'Gentle Breeze' is hardy in USDA Zone 4.

BRIEF DESCRIPTION OF THE PHOTOGRAPHS

The accompanying color photographs illustrate the overall appearance of the new *Miscanthus* variety 'Gentle Breeze' showing colors as true as it is reasonably possible to obtain in colored reproductions of this type. Colors in the photographs may differ from the color values cited in the detailed botanical description, which accurately describe the actual colors of the new variety 'Gentle Breeze'. The photographs are taken from plants which have been container-grown outdoors in Santa Barbara, Calif.

BOTANICAL DESCRIPTION OF THE PLANT

Figure 1:
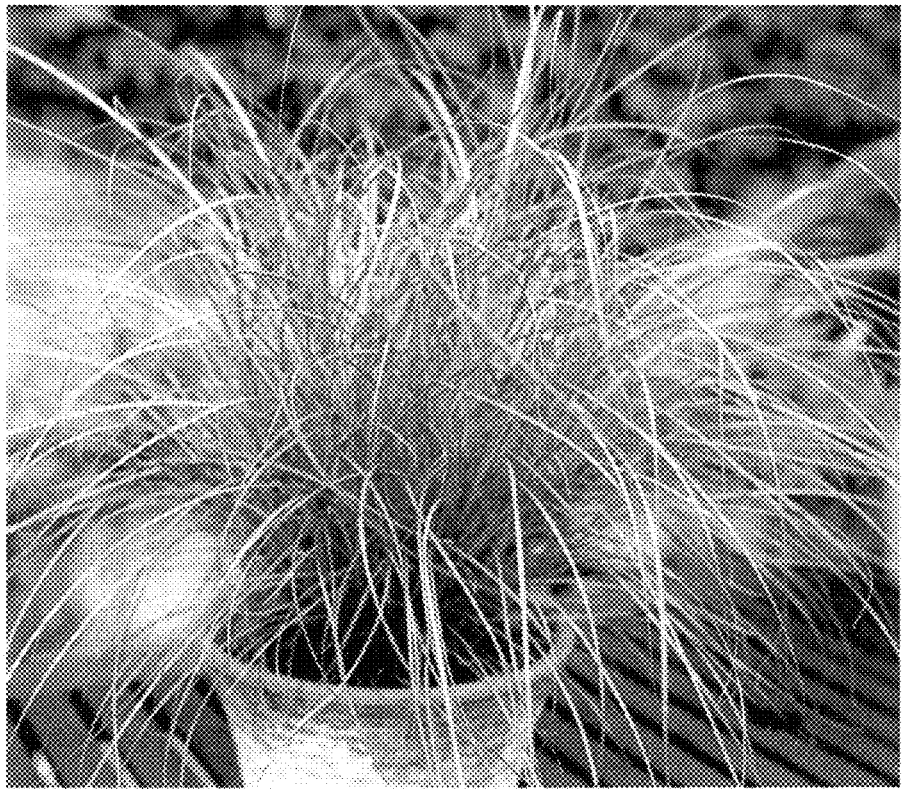
FIG. 1 depicts a two years old container-grown plant of 'Gentle Breeze' in early summer.
Figure 2:
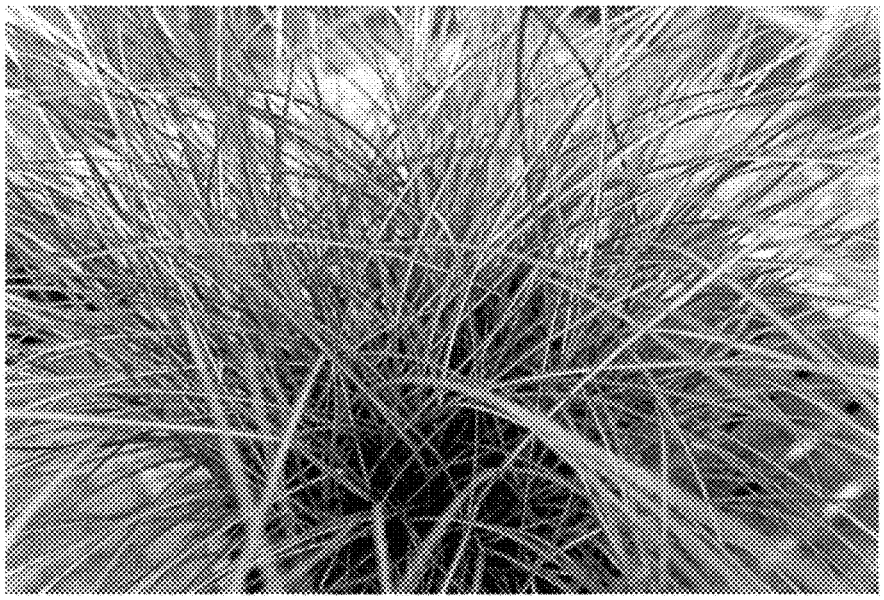
FIG. 2 depicts a close-up view of the bicolored foliage of 'Gentle Breeze' in early summer, showing the white to pale green central longitudinal stripe between two mid-green marginal bands.
Figure 3:
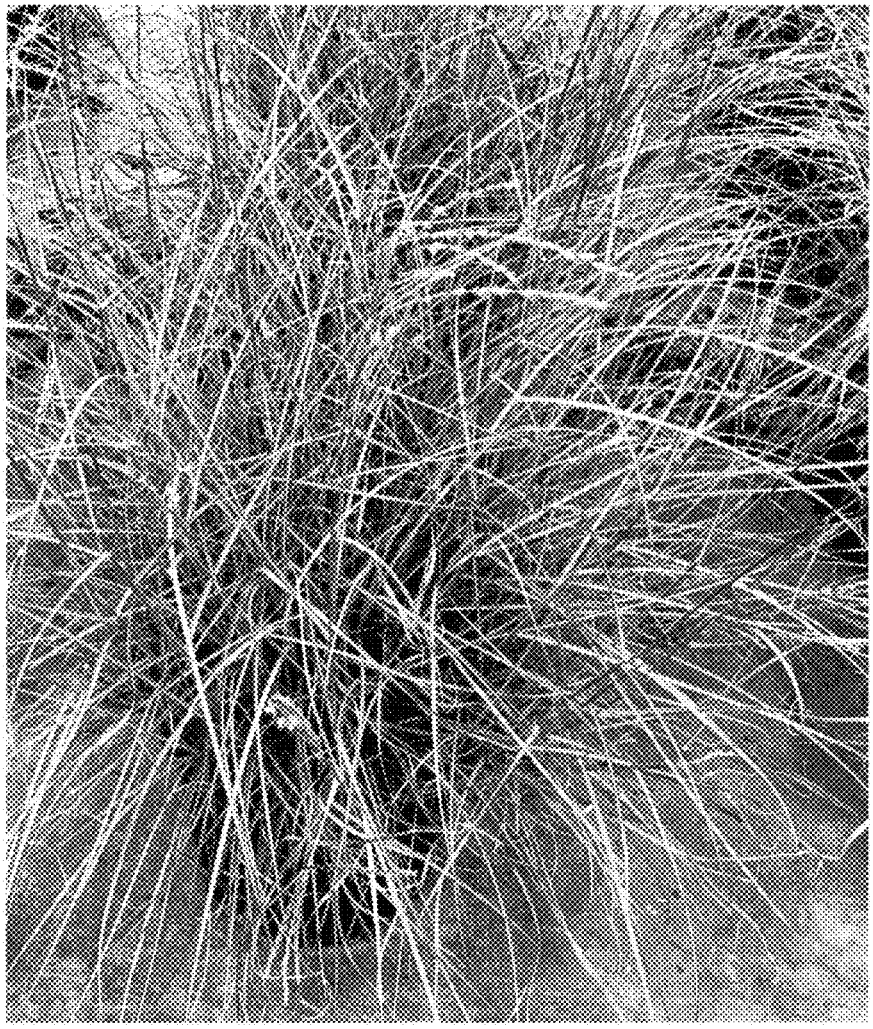
FIG. 3 depicts the late summer onset of mauve and eventually dark red foliage of 'Gentle Breeze', and the panicles of flowers.

The following is a detailed botanical description of 'Gentle Breeze' which has been prepared from observations and measurements of a two year old plant of 'Gentle Breeze' growing in a 2-gallon container in Santa Barbara, Calif. Color determinations are made in accordance with the 2007 edition of The Royal Horticultural Society Colour Chart, London, England, except where general color terms of ordinary dictionary significance are used. The growing requirements of 'Gentle Breeze' are similar to the species *Miscanthus sinensis*.

Botanical classification:

*Family*.—Poaceae.

*Genus*.—*Miscanthus*.

*Species*.—*Sinensis*.

*Common name*.—Maiden Grass.

*Variety*.—'Gentle Breeze'.

Parentage: Open pollination involving unknown parents within the inventor's garden collection of *Miscanthus* varieties.

Plant description:

*Growth habit*.—Upright plant habit with arching foliage.

*Commercial category*.—Ornamental grass.

*Use*.—For garden and landscape.

*Suitable container sizes*.—1 gallon container or larger.

*Propagation method*.—Division of established in-ground or container-grown plants; tissue culture.

*Rooting system*.—Fibrous.

*Crop time*.—From planting a rooted division or a rooted tissue culture young plant, 8-10 weeks to fill out in a 1-gallon container, 12-16 weeks for the plant to come into flower. Larger containers require a longer period of growth in order to fill out.

*Plant dimensions*.—A one year old plant established in a 2-gallon container is 1.1 m in height including the flowers and 40 cm in width. Older plants in the landscape retain same height and become wider with additional clumping.

*Cultural requirements*.—Grow in full sun and well-draining porous soil, with moderate water.

*Hardiness*.—USDA Zone 4.

Culms (stems):

*Description*.—Cane-like with nodes at which culm may bend and change color.

*Number*.—6-10 culms per plant.

*Dimensions* (*soil level to base of panicle*).—90 cm in length and 4 mm-6 mm in diameter.

*Shape*.—Cylindrical, hollow, white pithy interior.

*Culm internode distance*.—15-20 cm.

*Color* (*except lowest culm section*).—147C with anthocyanin pigmentation on solar-facing surface, anthocyanin color N186C.

*Color* (*lowest culm section from soil level to first node*).—Pale yellow-green, 150C.

*Surface*.—Glabrous and matte, except lowest culm section glabrous and glossy.

Foliage:

*Leaves quantity*.—8-10 leaves per fully developed flowering culm.

*Leaf aspect*.—Initially upright then arching and reflexing.

*Attachment*.—Sheathing at base.

*Sheath*.—5 cm-8 cm in length, 6 mm in width, scarious, 163D, falls away as plant matures leaving yellow exposed stem color 150C below first culm node.

*Leaf shape*.—Sulcate, upper surface concave.

*Leaf dimensions*.—50 cm-80 cm in length, 7 mm in width at base, 4 mm in width towards apex.

*Leaf margin*.—Sharply minutely serrate.

*Leaf surface* (*both surfaces*).—Glabrous.

*Leaf color until late summer* (*adaxial surface*).—Longitudinally striped, central sulcate band ranges between NN155D and 157D, outer marginal bands 143A-143B.

*Leaf color until late summer* (*abaxial surface*).—143A-143B.

*Leaf color beginning in late summer and in the fall* (*both surfaces*).—Increasing transition to 182C and finally to 187C.

*Leaf apex*.—Acute.

*Leaf base*.—Truncate.

*Venation pattern*.—Parallel.

*Midrib* (*adaxial surface*). Inconspicuous in central sulcate band of adaxial surface.

*Midrib* (*abaxial surface*).—Raised, color 157D.

Inflorescence:

*Peduncle* (*above uppermost culm node to base of panicle*).—Shape: Cross section elliptic. Dimensions: Up to 20 cm in length, 1.5-2.0 mm in width. Texture: Stiff, wiry, glabrous. Color: 147C with anthocyanin pigmentation on solar-facing surface, anthocyanin color N186C.

*Type*.—Terminal fan-like panicle, flowering from July to October, florets persistent.

*Panicle appearance*.—Plumose, consisting of 3-5 racemes arising from common base. Shorter racemes consist of approximately 40-50 spikelets, longer racemes bear 75-90 spikelets.

*Panicle dimensions*.—Length (base of lowest raceme to apex of highest raceme: 19 cm. Width of panicle 3 cm-5 cm.

*Raceme dimensions*.—Ranging between 5.5 cm and 19 cm in length, 6 mm in width.

*Raceme rachis color*.—143B

*Panicle color overall* (*predominantly the color of the spikelet glumes*).—Ranges between light mauve 64C (developing racemes) to light grey-brown or silver white 199D-156D (mature racemes).

*Spikelet description*.—Spikelets borne in pairs, one short (on short pedicel) and one longer (on longer pedicel). Florets consist of pairs of glumes, lemmas and paleas and one markedly protruding awn.

*Spikelet dimensions*.—Up to 6 mm in length (excluding pedicel, excluding awn), 2 mm in width.

*Spikelet pubescence*.—Numerous basal and very fine white hairs at base and surrounding the floret and 2 mm longer than floret, color NN155C.

*Pedicel*.—2 mm-4 mm in length, 0.5 mm in diameter, color 143B.

*Floret dimensions* (*arrangement of glumes, lemmas and paleas*).—5 mm in length, 2 mm in width).

*Glumes*.—2 (1 upper, 1 lower). Shape: Lanceolate, inwardly curved, apex acute, base cuneate, ciliate margin. Dimensions: 2 mm-5 mm in length, 2 mm in width. Texture: Scarious. Color: Ranging between 64C and 199D-156D.

*Lemmas*.—2 (1 upper fertile lemma bearing the awn, 1 lower sterile lemma). Shape: Lanceolate, inwardly curved, lower lemma apex acute, upper lemma apex notched, base truncate, ciliate margin. Dimensions: 3 mm-4 mm in length, 1.5 mm in width. Texture: Scarious. Color: 162B.

*Awn*.—Long, up to 12 mm in total length, protruding 5-7 mm beyond lemma apex, fine, wiry, bent or twisted, smooth, color predominantly NN155C, occasionally 156D or 161D.

*Paleas*.—Shape: Lanceolate, inwardly curved, apex acute, base truncate, ciliate margin. Dimensions: 2 mm-mm in length, 1.0-1.5 mm in width. Texture: Scarious. Color: 162B.

Reproductive organs:

*Stamens*.—3 in number, filaments 2 mm to 3 mm in length, 0.2 mm in diameter, color NN155D.

*Anthers*.—2 mm in length, less than 0.5 mm in width, color 200D.

*Pistil quantity*.—1.

*Stigma*.—2 in number, shape plumose, color 200A.

*Pollen*.—Not observed

*Ovary*.—Superior, rounded, 1 mm in diameter.

Seed: One seed per floret, capsule in shape, 1.5 mm in length, 0.75 mm in diameter, color 161D.

Diseases and pests: None known to the inventor.

COMPARISON WITH CLOSEST KNOWN VARIETIES

The inventor considers that the seed-raised species *Miscanthus purpurescens* and the named variety *Miscanthus* 'Adagio' (unpatented) are similar and different from 'Gentle Breeze' as follows.

Both 'Gentle Breeze' and the species *Miscanthus purpurescens* bear deep red foliage in the fall. However, *Miscanthus purpurescens* grows to a height of 1.75 m, whereas 'Gentle Breeze' is lower growing at a height of 1.1 m. In addition, the inventor has observed that older plants of *Miscanthus purpurescens* will split apart, whereas 'Gentle Breeze' remains compact and tight and upright.

Both 'Gentle Breeze' and 'Adagio' are low-growing varieties. However, 'Adagio' does not develop any red coloration at any stage of its growth, whereas 'Gentle Breeze' develops dark red foliage in the fall.

'Gentle Breeze' may also be compared with the inventor's variety *Miscanthus* 'Fire Dragon' (U.S. Plant Pat. No. 30,374). Whereas both 'Gentle Breeze' and 'Fire Dragon' bear red colored foliage in the fall, 'Fire Dragon' is considerable larger in size at 2.2 m in overall height as compared with 'Gentle Breeze' whose height when established is 1.1 m. In addition, the foliage of 'Gentle Breeze' is more slender.

'Gentle Breeze' may also be compared with the inventor's variety *Miscanthus* 'Little Miss' (U.S. Plant Pat. No. 28,849). Whereas 'Gentle Breeze' first exhibits its red foliage coloration in late summer, 'Little Miss' develops its fall color earlier in the season, in April or May.

I claim:

1. A new and distinct cultivar of *Miscanthus* plant named 'Gentle Breeze' as described and illustrated herein.

* * * * *